United States Patent
Lam et al.

(10) Patent No.: US 11,609,326 B2
(45) Date of Patent: Mar. 21, 2023

(54) TRANSPARENT ULTRASOUND TRANSDUCER WITH LIGHT BEAM SHAPING AND THE METHOD FOR ASSEMBLING THE SAME

(71) Applicant: THE HONG KONG POLYTECHNIC UNIVERSITY, Hong Kong (CN)

(72) Inventors: Kwok Ho Lam, Hong Kong (CN);
Riqiang Lin, Hong Kong (CN);
Dongliang Shi, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 0 days.

(21) Appl. No.: 17/302,703

(22) Filed: May 11, 2021

(65) Prior Publication Data
US 2022/0365209 A1    Nov. 17, 2022

(51) Int. Cl.
*G01S 15/89* (2006.01)
*G10K 11/30* (2006.01)
*G02B 3/00* (2006.01)

(52) U.S. Cl.
CPC .......... *G01S 15/8968* (2013.01); *G10K 11/30* (2013.01); *G02B 3/0087* (2013.01)

(58) Field of Classification Search
CPC .... G01S 15/8968; G10K 11/30; G02B 3/0087
See application file for complete search history.

(56) References Cited

U.S. PATENT DOCUMENTS 10,905,397 B2 * 2/2021 Yang .................... A61B 5/0095
2005/0187471 A1 * 8/2005 Kanayama ........... A61B 5/0091
600/437

(Continued)

FOREIGN PATENT DOCUMENTS

| CN | 112914508 A | * | 6/2021 | |
| WO | 2020167870 A1 | | 8/2020 | |
| WO | WO-2020167870 A1 | * | 8/2020 | ........... A61B 5/0095 |

OTHER PUBLICATIONS

Graham W. J. Brodie et al., "Optically Transparent Piezoelectric Transducer for Ultrasonic Particle Manipulation," IEEE Transactions on Ultrasonics, Ferroelectrics, and Frequency Control, vol. 61, No. 3, Mar. 2014.

(Continued)

*Primary Examiner* — Daniel Pihulic
(74) *Attorney, Agent, or Firm* — S&F/WEHRW

(57) ABSTRACT

A transparent ultrasound transducer device for multi-mode optical imaging on a target is provided. The device includes a transparent piezoelectric transducer, one or more wires, and an optical lens. The transparent piezoelectric transducer of a first acoustic impedance is configured to receive acoustic waves from the target. The transparent piezoelectric transducer has a first surface and a second surface. The first surface and the second surface are coated with transparent electrically conductive coatings. The optical lens is contacted with and optically coupled to the first surface of the transparent piezoelectric transducer. The optical lens is made of a material with a second acoustic impedance, and the first and second acoustic impedances are substantially similar to minimize an acoustic impedance mismatch such that sensitivity of the device is improved.

19 Claims, 5 Drawing Sheets

(56) References Cited

U.S. PATENT DOCUMENTS

2018/0228464 A1* 8/2018 Yang .................... A61B 5/0062
2022/0133273 A1* 5/2022 Dangi .................. A61B 5/0095
600/459

OTHER PUBLICATIONS

Ajay Dangi et al., "Lithium niobate-based transparent ultrasound transducers for photoacoustic imaging," Optical Society of America, Optics Letters, col. 44, No. 21, Nov. 1, 2019.
Ruimin Chen et al., "Transparent High-Frequency Ultrasonic Transducer for Photoacoustic Microscopy Application," IEEE Transactions on Ultrasonics, Ferroelectrics, and Frequency Control, vol. 67, No. 9, Sep. 2020.
Cheng Fang et al., "A Focused Optically Transparent PVDF Transducer for Photoacoustic Microscopy," IEEE Sensors Journal, vol. 20, No. 5, Mar. 1, 2020.
T. Wang et al., "Multiparametric photoacoustic microscopy of the mouse brain with 300-kHz A-line rate," Neurophotonics, vol. 3, No. 4, 2016, Art. no. 045006.
Hu, S., et al., "Second-Generation Optical-Resolution Photoacoustic Microscopy with Improved Sensitivity and Speed," Optics Letters, vol. 36, No. 7, Apr. 1, 2011, pp. 1134-6.

* cited by examiner

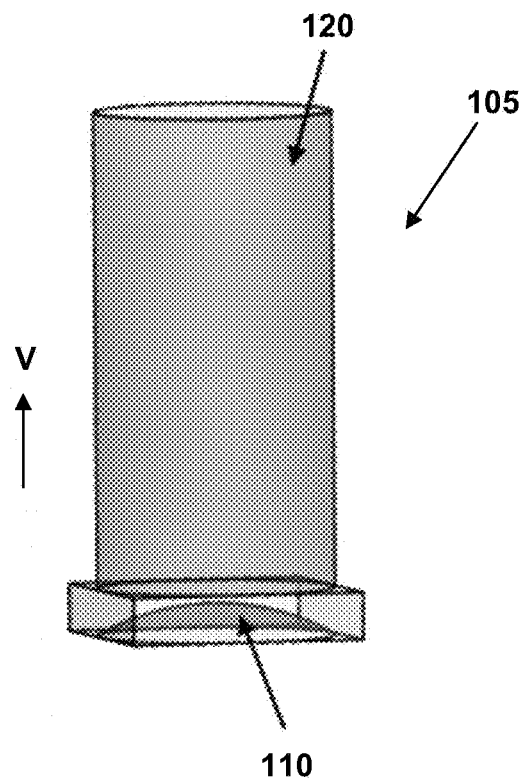 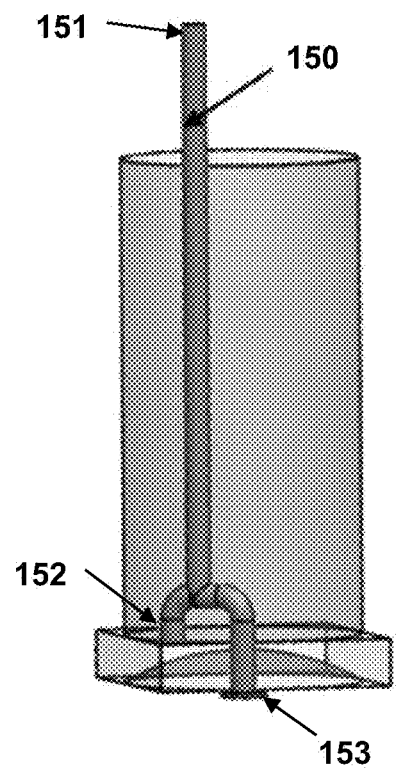
FIG. 4A
FIG. 4B
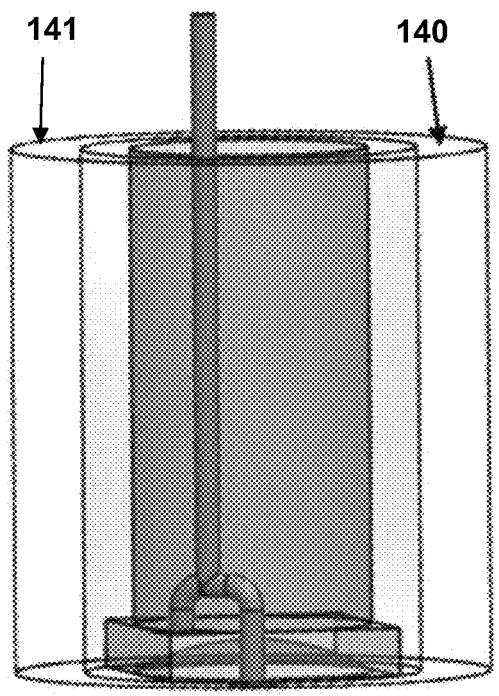 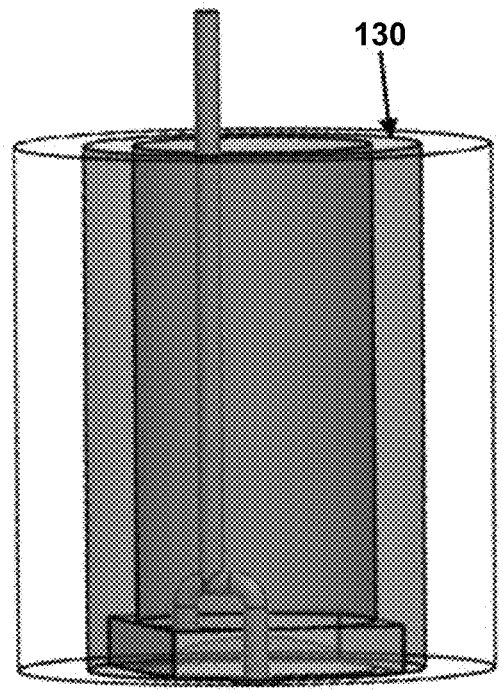
FIG. 4C
FIG. 4D

TRANSPARENT ULTRASOUND TRANSDUCER WITH LIGHT BEAM SHAPING AND THE METHOD FOR ASSEMBLING THE SAME

LIST OF ABBREVIATIONS

GRIN Gradient-index
ITO Indium tin oxide
LED Light emitting diode
LNO Lithium niobate ($LiNbO_3$)
OCT Optical coherence tomography
PA signal Photoacoustic signal
PAM Photoacoustic microscopy
PMN-PT Lead magnesium niobate/Lead titanate
PVDF Polyvinylidene fluoride
TUST Transparent ultrasound transducer

FIELD OF THE INVENTION

The present disclosure generally relates to the technical field of imaging and biomedical imaging, and particularly relates to a TUST device that is capable of shaping the light beam for multi-mode imaging system for multi-mode optical imaging.

BACKGROUND OF THE INVENTION

In the field of biomedical imaging, PAM is an imaging method based on the photoacoustic effect, which combines optical illumination and acoustic detection to achieve high-resolution images at greater depths. In order to perform PAM, an excitation light beam is generated and focused on the body tissue. The optical energy absorbed is converted to acoustic waves due to the transient thermoelastic expansion of light-absorbing molecules. Accordingly, the acoustic waves are transmitted and detected by piezoelectric transducers. In the event that the light source and the ultrasonic receiver must be positioned on the same side of the body tissue, the integration of light beams and acoustic waves in the same imaging system can be challenging and requires both optical and acoustic components. However, the commonly used ultrasound transducers are made of optically opaque materials and may completely block the light transmission. On the other hand, the optical components have a higher acoustic impedance than the air, which may reflect or scatter the acoustic signals and lower the signal amplitude.

To address this problem, there are proposals of delivering the light to the body tissue by bending the beam around the ultrasound transducer using prisms or mirror [6], or through an opening of a hollow or ring-shaped transducer [5]. However, the complexity in the structure and the beam geometries may be challenging to make with less design feasibility and detrimental to the overall performance.

There are some TUST devices proposed as well. The first TUST device was introduced in 2014 by Brodie et al. [1], which is shown in FIG. 1A. The optically transparent TUST device is coated with ITO on a wafer of LNO single crystal for ultrasonic particle manipulation. Despite the early effort in exploiting the use of the optically transparent LNO for the PAM purposes, the proposal was not supported with a well-defined acoustic focal point, and the TUST device does not provide an optimal detection condition for the PA signal.

Another TUST device for low-frequency (14.5 MHz) applications was introduced by Dangi et al. [2] in 2019, and filed as International patent WO 2020167870 A1. A 2.5 mm×2.5 mm transparent photoacoustic transducer 30 having a copper housing 20 and integrated with an optical fiber 10 is shown in FIG. 1B. The TUST device was fabricated by coating the top and bottom surface of LNO with transparent ITO electrodes. The resulting TUST device showed >80% optical transparency in the selected wavelength range and the reflected photoacoustic images were formed by raster scanning. The TUST device is unfocused, so the unfocused light beam leads to a low resolution of imaging.

Ruimin et al. [3] developed another TUST device for high-frequency (36.9 MHz) applications, as shown in FIG. 1C. The TUST device used LNO single crystal and ITO electrodes and achieved up to 90% optical transmission in the visible-to-near-infrared spectrum. In particular, the TUST device comprises a parylene thin-film, an insulating and optically transparent epoxy for backing, and a transparent LNO with ITO electrodes, which were mounted to a brass housing.

Another example of the TUST device was proposed by Fang et al. [4] and shown in FIG. 1D. In the paper, a focused TUST device using PVDF film coated with ITO and metal electrodes was described. The TUST device had an optical transmittance of 60% (532 nm) with the advantages of easier alignment of the optical excitation and acoustic focal points, and compact configuration. However, it is difficult to fabricate the TUST device with a small aperture (e.g., <2 mm) because of its very low dielectric constant.

With the foregoing development of a TUST device for PAM based on photoacoustic effect, all the TUST structures proposed did not inherently combine with any optical elements. Therefore, the TUST devices were required to combine with an optical imaging system, necessitating more room to fix the optical imaging system thereto. Moreover, opaque metal housings were employed on the TUST devices, which limited some applications of the TUST devices, particularly in performing multi-mode imaging.

As ultrasound imaging has been widely used, especially in clinical diagnosis. Ultrasound imaging can be used for breast cancer detection, intravascular atherosclerotic plaque detection, gastrointestinal tumor detection and vaginal disease detection, etc. However, the diagnostic information obtained using a sole imaging mode is limited. In recent years, more and more multi-modal imaging systems have been developed in the hope of providing more comprehensive information for clinical diagnosis. The conventional devices are usually very complicated because of the optically opaque ultrasound transducers.

Accordingly, there is a need in the art for a TUST device that seeks to address at least some of the above problems and limitations encountered in PAM. Furthermore, other desirable features and characteristics will become apparent from the subsequent detailed description and the appended claims, taken in conjunction with the accompanying drawings and this background of the disclosure.

SUMMARY OF THE INVENTION

Provided herein are a TUST device for performing biomedical imaging. It is an objective of the present disclosure to provide an entirely transparent TUST device that is capable of shaping the light beam for multi-mode imaging system.

The TUST device comprises a transparent piezoelectric transducer of a first acoustic impedance, one or more wires, and an optical lens. The transparent piezoelectric transducer is configured to receive acoustic waves from the target, wherein the transparent piezoelectric transducer comprises a first surface and a second surface. The first surface and the second surface are coated with transparent electrically conductive coatings. The one or more wires connect the first surface and the second surface to external connectors. The optical lens contacts with and optically couples to the first surface of the transparent piezoelectric transducer as a backing material for transmitting a light beam to the target. The optical lens is made of a material with a second acoustic impedance. The first and second acoustic impedances are substantially similar to minimize an acoustic impedance mismatch such that sensitivity of the device is improved.

In certain embodiments, the optical lens is a GRIN lens. The GRIN lens is designed for shaping the light beam as a focusing beam, a collimating beam, or a diverging beam by varying an index of refraction.

In certain embodiments, the second surface is a concave surface with a radius of curvature determined based on a focal length for focusing the acoustic waves from the target and emitting the focused acoustic waves from the TUST device.

In certain embodiments, the TUST device further comprises a transparent housing arranged to house a transducer unit formed by contacting the optical lens to the first surface of the transparent piezoelectric transducer, wherein the transparent housing is made of transparent materials, like glass or acrylic.

In yet another embodiments, a method for assembling a TUST device for multi-mode optical imaging on a target is disclosed. The TUST device comprises a transparent piezoelectric transducer having a first surface and a second surface, and an optical lens. The method includes the steps of: (1) processing a piezoelectric substrate to form the second surface with a concave surface; (2) coating the first surface and the second surface with transparent electrically conductive coatings; (3) contacting the optical lens with the transparent piezoelectric transducer to obtain a transducer unit; and (4) connecting one or more wires from the first surface and the second surface to external connectors.

In certain embodiments, the method further includes (5) assembling the transducer unit into a transparent housing; and (6) filling a gap between the transparent housing and the transducer unit with a transparent epoxy resin.

In certain embodiments, the step of processing the piezoelectric substrate to form the second surface with the concave surface further comprises polishing the piezoelectric substrate to obtain the concave surface with a radius of curvature determined based on a focal length for focusing the acoustic waves from the target and emitting the focused acoustic waves from the TUST device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which:

FIG. 4A depicts the first step for fabricating the TUST device of FIG. 2, in accordance with embodiments of the present disclosure;

FIG. 4B depicts second step for fabricating the TUST device of FIG. 2, in accordance with embodiments of the present disclosure;

FIG. 4C depicts third step for fabricating the TUST device of FIG. 2, in accordance with embodiments of the present disclosure;

FIG. 4D depicts fourth step for fabricating the TUST device of FIG. 2, in accordance with embodiments of the present disclosure;

DETAILED DESCRIPTION OF THE INVENTION

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The benefits, advantages, solutions to problems, and any element(s) that may cause any benefit, advantage, or solution to occur or become more pronounced are not to be construed as a critical, required, or essential features or elements of any or all of the claims. The invention is defined solely by the appended claims including any amendments made during the pendency of this application and all equivalents of those claims as issued.

The term "light beam," as used herein, refers to any beams of electromagnetic radiation including, but not limited to, visible light, ultraviolet, infrared, and microwave. The light beam may be generated by a light source, such as a laser (single wavelength laser or multi-wavelength laser), a laser diode, an LED, or a microwave generator. In certain embodiments, the light source may be provided through an optical fiber. Combinations of two or more types of light sources may be used. The light source may emit light beam having a predetermined range of wavelength. For example, the light beam may have a wavelength ranging between 400 nm to 2000 nm. In another example, the light beam may have a wavelength ranging between 400 nm to 700 nm.

Figure 1A:
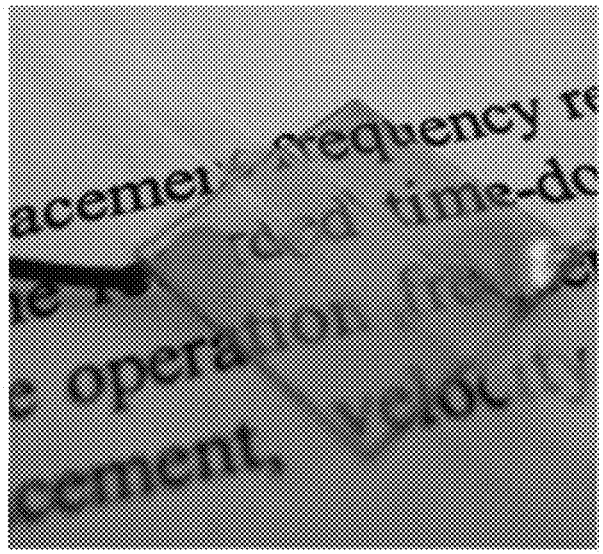
FIG. 1A is a photo of the TUST device in accordance with the disclosure of Brodie et al. [1]
Figure 1B:
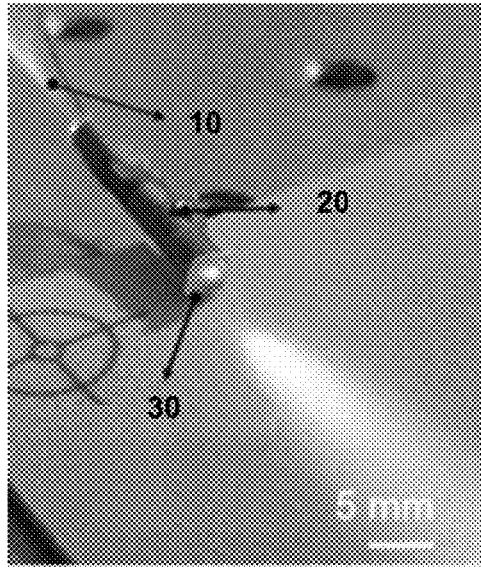
FIG. 1B is a photo of the LNO-based TUST device in accordance with the disclosure of Dangi et al. [2]
Figure 1C:
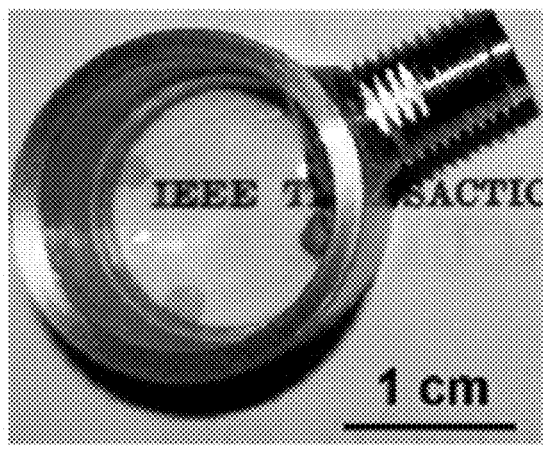
FIG. 1C is a photo of the high-frequency TUST device in accordance with the disclosure of Chen et al. [3]
Figure 1D:
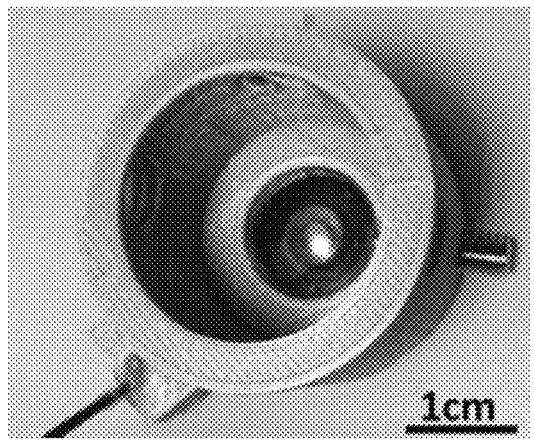
FIG. 1D is a photo of the focused TUST device using PVDF film in accordance with the disclosure of Fang et al. [4]
Figure 2:
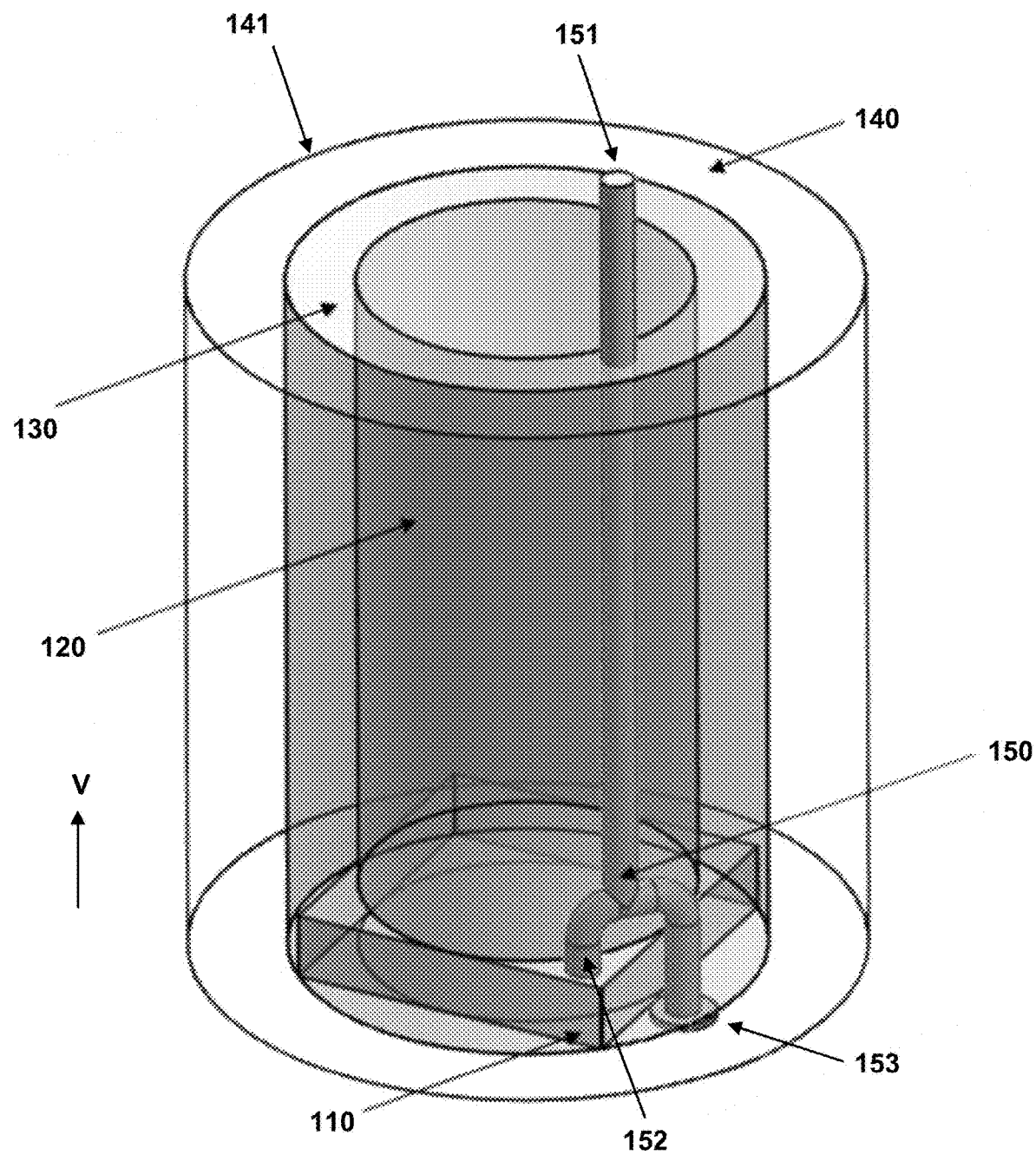
FIG. 2 depicts a perspective view of a TUST device, in accordance with embodiments of the present disclosure.

Terms such as "inner," "outer," "outermost," "top," "bottom," and variations thereof are used herein for ease of description to explain the positioning of an element, or the positioning of one element relative to another element, and are not intended to be limiting to a specific orientation or position. A vertical axis V is defined by the gravity as shown in FIG. 2, extending from the bottom of the TUST device 100 to the top of the TUST device 100. Terms such as "first," "second," and variations thereof herein are used to describe various elements, regions, sections, etc. and are not intended to be limiting.

Terms such as "connected," "attached," "coupled," and variations thereof are used broadly and encompass direct and indirect connections, attachments, and mountings; and are not restricted to electrical, physical, optical, or mechanical connections, attachments, or mountings.

The present disclosure generally relates to the technical field of imaging and biomedical imaging. More specifically, but without limitation, the present disclosure relates to a TUST device 100 that is capable of shaping the light beam for a multi-mode imaging system to provide multi-mode optical imaging. In certain embodiments, the multi-mode optical imaging includes photoacoustic imaging and OCT imaging. It is apparent that the present disclosure may be applied to other combined optical-acoustic imaging without departing from the scope and spirit of the present disclosure. With reference to FIG. 2, the TUST device 100 may be embodied as an optically transparent and compact device comprising a transparent piezoelectric transducer 110, an optical lens 120, a transparent epoxy resin 130, a transparent housing 140, and a wire 150.

The TUST device 100 is configured to perform multi-mode optical imaging, particularly photoacoustic imaging, on a target and receive acoustic waves therefrom. The target and the acoustic wave are respectively designated as 300 and 230 in FIGS. 5A-5C. The target 300 may be a human body, a human organ, a fetus, a non-organic object inside a human body, an animal, an animal organ, a non-organic object inside an animal, or any object (living or non-living) that can absorb an optical energy and convert the optical energy to acoustic waves 230 by the transient thermoelastic expansion. The TUST device 100 is used to perform PAM, which essentially provides optical illumination of an excitation signal, in the form of a light beam, and focuses the light beam to the target. The excitation signal is absorbed by the target 300 and converted to acoustic waves 230 by the transient thermoelastic expansion of the light-absorbing molecules in the target 300, thereby the acoustic waves 230 are transmitted back to the TUST device 100 for detection by the transparent piezoelectric transducer 110.

Figure 3A:
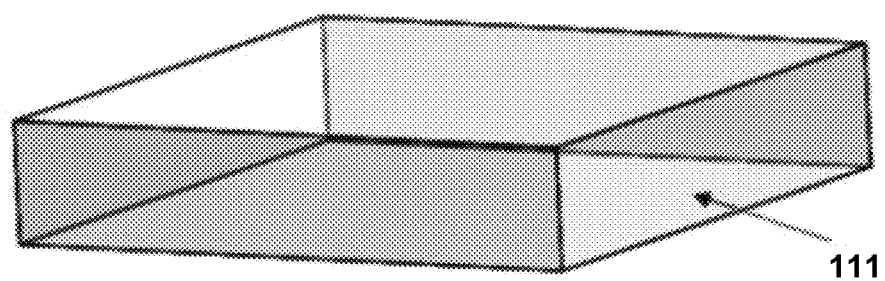
FIG. 3A depicts the first step for preparing the transparent piezoelectric transducer, in accordance with embodiments of the present disclosure.
Figure 3B:
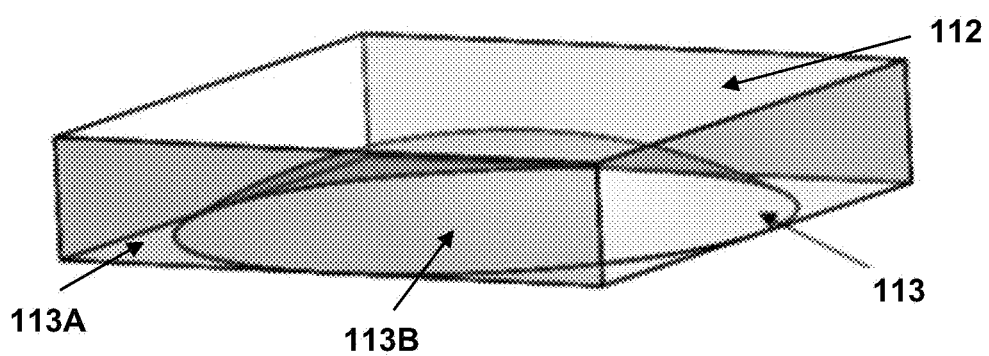
FIG. 3B depicts the second step for preparing the transparent piezoelectric transducer, in accordance with embodiments of the present disclosure.
Figure 3C:
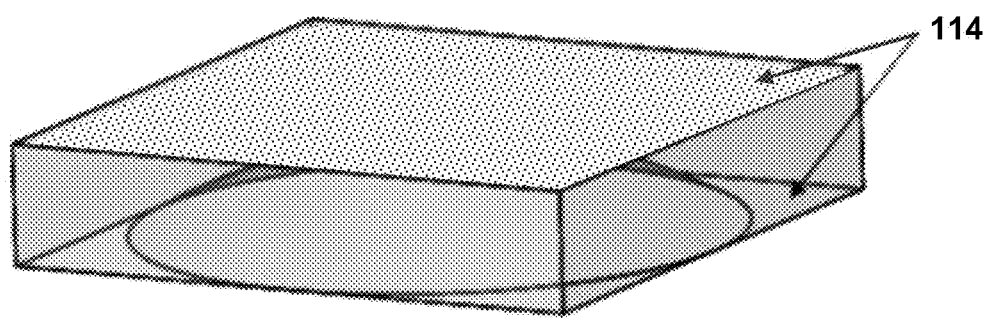
FIG. 3C depicts the third step for preparing the transparent piezoelectric transducer, in accordance with embodiments of the present disclosure.

The transparent piezoelectric transducer 110 is arranged to receive, from the target 300, the photoacoustic response in the form of acoustic waves 230 generated by the transient thermoelastic expansion. The transparent piezoelectric transducer 110 is preferably made of LNO, and in certain embodiments, can be made of other transparent material such as PVDF, PMN-PT, transparent polymers, transparent ceramics, or single crystal LNO. For single crystal LNO, the transparent piezoelectric transducer 110 has a first acoustic impedance typically around 34.1 MRayls. For PMN-PT, the first acoustic impedance is typically around 30.85 MRayls. For PVDF, the first acoustic impedance is around 3.8 MRayls. FIGS. 3A-3C show the steps for preparing the transparent piezoelectric transducer 110.

To prepare the transparent piezoelectric transducer 110, a piezoelectric substrate 111, also referred to as a transparent piezoelectric wafer, may be used. The transparent piezoelectric transducer 110, or so do the piezoelectric substrate 111, comprises a first surface 112 and a second surface 113. This is illustrated in FIG. 3B. The first surface is a flat surface and is generally referred to as the back side of the transparent piezoelectric transducer 110. The second surface 113 has a concave surface 113B and is generally referred to as the front side of the transparent piezoelectric transducer 110. As it is apparent that the terms "front" and "back", as used herein, are only referring to the respective proximity to the target, and are not intended to be limiting to a specific orientation or position.

The concave surface 113B of the second surface 113 is generally smooth and continuous with a radius of curvature determined based on a focal length for focusing the acoustic waves from the target 300 and emitting the focused acoustic waves from the TUST device 100. In certain embodiments, the peripheries 113A of the concave surface 113B are smooth and flat. The piezoelectric substrate 111 is processed on the front side to form the second surface 113 with the concave surface 113B and the peripheries 113A. In contrast, the first surface 112 is substantially smooth throughout. The term "smooth" means that the surface is substantially free of protrusions, dips, or the like. In practice, the concave surface of the second surface 113 is very difficult to fabricate because of the fragile nature of the piezoelectric substrate 111. The present disclosure provides a method for obtaining the concave surface 113B by polishing the piezoelectric substrate 111. It is apparent that the step of polishing can also be accomplished by various means and methods without departing from the scope and spirit of the present disclosure. The resulting concave surface obtained can focus on a position defined by the radius of curvature for receiving the acoustic waves 230.

The first surface 112 and the second surface 113 may be coated with transparent electrically conductive coatings 114 to obtain the transparent piezoelectric transducer 110, as conceptually illustrated in FIG. 3C. Preferably, the transparent electrically conductive coatings 114 are made of ITO. In some other cases, tin oxide, indium oxide, zinc oxide, or any combination thereof may also be used. After coating, the first surface 112 can be considered as a first transducer electrode, and the second surface 113 can be considered as a second transducer electrode. The two transducer electrodes are physically and electrically separated. Optionally, a shield wire may be added between the two transducer electrodes to prevent forming any short-circuit path.

With reference to FIGS. 4A-4D, the steps for fabricating the TUST device 100 are illustrated in accordance with the present disclosure. The optical lens 120 is arranged to contact with and optically coupled to the transparent piezoelectric transducer 110 along a vertical axis V as a backing material to obtain a transducer unit 105. In one embodiment, the contact is secured firmly by adhesively attaching the optical lens 120 to the first surface 112 of the transparent piezoelectric transducer 110. The optical lens 120 is acted as a backing layer of the transducer unit 105. In certain embodiments, the optical lens 120 is a GRIN lens, which is made of a material with a second acoustic impedance. As the material may be quartz, silica, or glass, the second acoustic impedance is typically around 11-16 MRayls. Advantageously, the first and second acoustic impedances of two materials are substantially similar to minimize an acoustic impedance mismatch such that the light passing through the optical lens 120 to the transparent piezoelectric transducer 110 has less reflection. Therefore, by using the optical lens 120 as a backing material, the sensitivity of the device 100 is improved and the signal-to-noise ratio of the transparent piezoelectric transducer 110 is very high. In contrast, conventionally an optically transparent epoxy is used as the backing material, which has an acoustic impedance of around 1-3 MRayls. Therefore, transparent epoxy has a higher acoustic impedance mismatch affecting the detection sensitivity.

Next, the transducer unit 105 is connected for enabling measurement of the acoustic waves 230 reflected from the target 300. In one embodiment, the transparent piezoelectric transducer 110 captures the photoacoustic responses. The one or more wires 150 are connected to the first surface 112 and the second surface 113 using electrically conductive glue, as shown in FIG. 4B. The amount of the electrically conductive glue should be properly controlled to avoid short-circuit between the first surface 112 and the second surface 113. The first surface 112 and the second surface 113 are respectively connected via a first terminal 152 and a second terminal 153 to external connectors (not shown) at a distal end 151. In one embodiment, the first terminal 152 is the positive terminal which is electrically connected to the first surface 112, and the second terminal 153 is the negative terminal which is electrically connected to the second surface 113. The one or more wires 150 may be, for example, nano silver wires, coaxial wires, insulated wires, twisted pair wires, or the like. The external connectors allow electric connection to a multi-mode optical imaging system for analyzing the acoustic response.

Refer to FIGS. 4C and 4D, the transducer unit 105 is assembled within a transparent housing 140. The transparent housing 140 is made of glass or acrylic or other transparent materials. The transparent housing 140 has a larger diameter than transducer unit 105, which is arranged to act as an outer protective layer for the transducer unit 105. Preferably, the TUST device 100 further comprises a parylene film 141 coated as an outermost layer covering the transparent housing 140. The parylene film 141 is a matching layer and a waterproof layer of the TUST device 100. In one embodiment, the TUST device 100 further comprises a transparent epoxy resin 130 filling a gap between the transparent housing 140 and the inner structure of the transducer unit 105. The transparent epoxy resin 130 is also transparent and provides extra support and protection to the transducer unit 105. During applying transparent epoxy resin 130 on the transducer unit 105, gas should be extracted from the transparent epoxy resin 130 to ensure vacuum in the gap for facilitating the curing the homogeneous transparent epoxy resin 130.

Figure 5A:
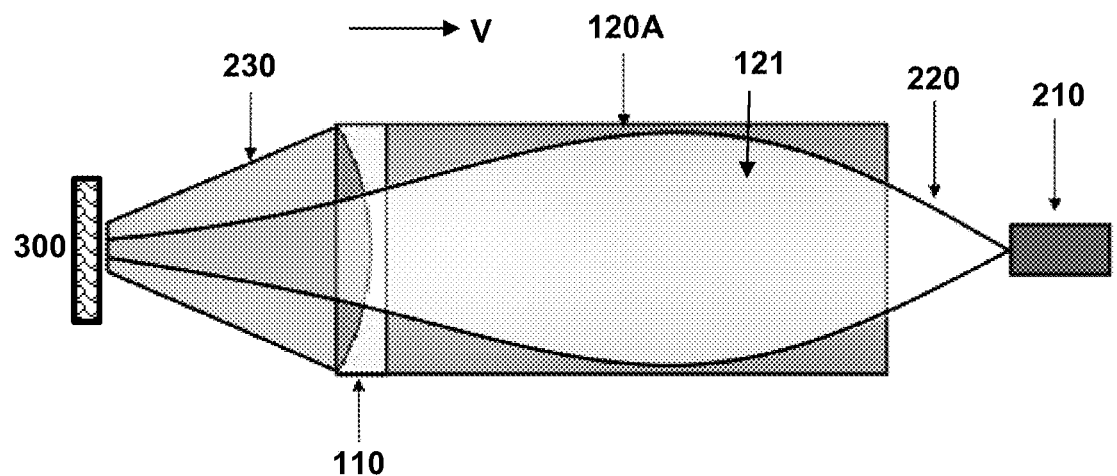
FIG. 5A depicts the operation of the TUST device of FIG. 2 for focusing a light beam, in accordance with embodiments of the present disclosure.
Figure 5B:
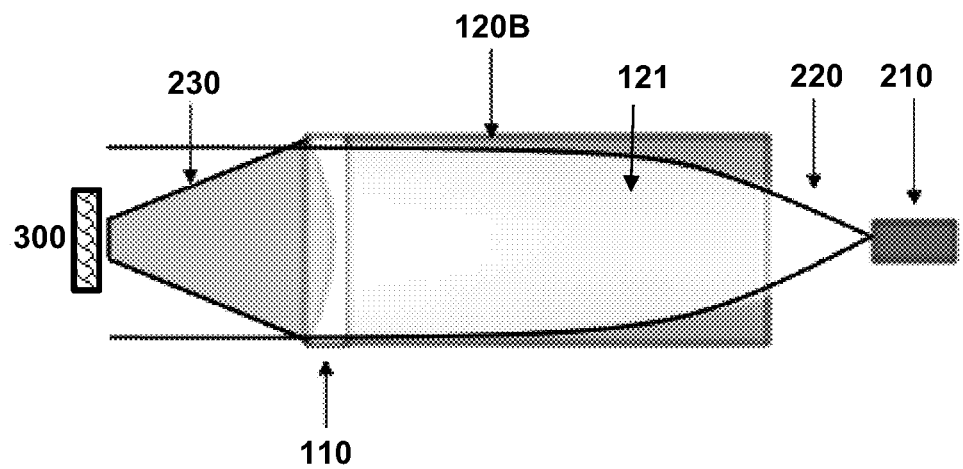
FIG. 5B depicts the operation of the TUST device of FIG. 2 for collimating a light beam, in accordance with embodiments of the present disclosure.
Figure 5C:
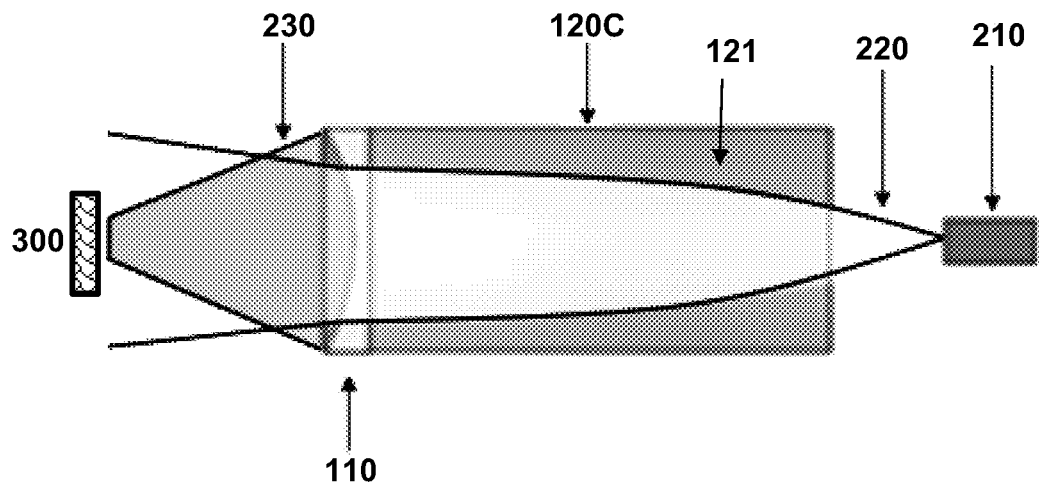
FIG. 5C depicts the operation of the TUST device of FIG. 2 for diverging a light beam, in accordance with embodiments of the present disclosure.

Another aspect of the present disclosure provides the use of the optical lens 120 for modifying the light beam 220 patterns transmitting out of the TUST device 100, which is illustrated in FIGS. 5A-5C. A light source 210 is configured to generate the light beam 220 to provide light illumination and excitation to the target 300. In certain embodiments, the light source 210 may include an optical fiber receiving light from an input end and emitting light from an output end. In some other embodiments, the light source 210 may comprise one or more LEDs or other light sources known in the art. The TUST device 100 of the present disclosure is substantially transparent (except for the one or more wirings 150), which allows at least 90% or approximately 100% of light in the defined wavelength range to pass through. This enables the TUST device 100 to be used for various optical imaging applications.

The optical lens 120 is configured to shape the light beam 220 by focusing, collimating, or diverging the light beam 220, which enables multi-mode imaging. In one embodiment, the optical lens 120 may comprise one or more optical elements selected from the group consisting of one or more mirrors, lens, collimators, prisms, diverging elements, and diffractive elements. Therefore, by properly arranging the optical elements, the optical lens 120 can be customized as a focusing lens 120A, a collimating lens 120B, or a diverging lens 120C. In another embodiment, the optical lens 120 can be a GRIN lens. As the GRIN lens affects the optical path by varying the index of refraction within the lens body 121 and a length of the lens body 121, the GRIN lens could be designed for shaping the light beam as a focusing beam, a collimating beam, or a diverging beam.

In certain embodiments, the optical lens 120 is customized as the focusing lens 120A, as illustrated in FIG. 5A. The incidental light beam 220 is refracted by the one or more optical elements into a focusing beam inside the lens body 121 to focus the light beam 220 accordingly to a predetermined focus point.

In another embodiment, the optical lens 120 is customized as the collimating lens 120B, as illustrated in FIG. 5B. The incidental light beam 220 is refracted by the one or more optical elements into a collimated beam inside the lens body 121 to collimate the light beam 220 and transmit out towards the target 300.

In yet another embodiment, the optical lens 120 is customized as the diverging lens 120C, as illustrated in FIG. 5C. The incidental light beam 220 is refracted by the one or more optical elements into a diverging beam inside the lens body 121 to diverge the light beam 220 and transmit out towards the target 300.

As illustrated, the TUST device 100 utilizes the optical lens 120 as the backing layer, which provides a higher acoustic impedance than the transparent epoxy resin conventionally used in the prior arts. The design is simple without the complicated and bulky configurations for combining the light and acoustic signals together. The entire device (except the one or more wires 150) is almost transparent, which allows the light beam 220 to pass through in different ways enabling multi-mode imaging. The nature of transparency also enables the TUST device 100 to combine with a variety of different optical imaging modes including white light imaging, photoacoustic imaging, optical coherence tomography, fluorescence imaging, and other imaging modes.

The above described the TUST device 100 is easy to manufacture and compatible with most commonly used ultrasound apparatuses and lighting devices to achieve high sensitivity multi-mode optical imaging. The TUST device 100 can be scalable to fit various applications and may come with different sizes and dimensions. In certain embodiments, the TUST device 100 may be mounted to different testing equipment, portable devices, tablet, or other measuring systems.

This illustrates the TUST device 100 that is capable of shaping the light beam 220 for multi-mode imaging system to provide multi-mode optical imaging in accordance with the present disclosure. It will be apparent that variants of the above-disclosed and other features and functions, or alternatives thereof, may be combined into many other devices. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

LIST OF REFERENCES

There follows a list of references that are occasionally cited in the specification. Each of the disclosures of these references is incorporated by reference herein in its entirety.
[1] Graham W. J. Brodie et al., "Optically Transparent Piezoelectric Transducer for Ultrasonic Particle Manipulation," IEEE Transactions on Ultrasonics, Ferroelectrics, and Frequency Control, vol. 61, no. 3, March 2014.
[2] Ajay Dangi et al., "Lithium niobate-based transparent ultrasound transducers for photoacoustic imaging," Optical Society of America, Optics Letters, col. 44, no. 21, Nov. 1, 2019.
[3] Ruimin Chen et al., "Transparent High-Frequency Ultrasonic Transducer for Photoacoustic Microscopy Application," IEEE Transactions on Ultrasonics, Ferroelectrics, and Frequency Control, vol. 67, no. 9, September 2020.
[4] Cheng Fang et al., "A Focused Optically Transparent PVDF Transducer for Photoacoustic Microscopy," IEEE Sensors Journal, vol. 20, no. 5, Mar. 1, 2020.
[5] T. Wang et al., "Multiparametric photoacoustic microscopy of the mouse brain with 300-kHz A-line rate," Neurophotonics, vol. 3, no. 4, 2016, Art. no. 045006.
[6] Hu, S., et al., "Second-Generation Optical-Resolution Photoacoustic Microscopy with Improved Sensitivity and. Speed," Optics Letters, vol. 36, no. 7, Apr. 1, 2011, pp. 1134-6.

What is claimed is:

1. A transparent ultrasound transducer device for multi-mode optical imaging on a target, the device comprising:
a transparent piezoelectric transducer of a first acoustic impedance configured to receive acoustic waves from the target, wherein the transparent piezoelectric transducer comprises a first surface and a second surface, and wherein the first surface and the second surface are coated with transparent electrically conductive coatings;
one or more wires connecting the first surface and the second surface to external connectors; and
an optical lens directly contacted with and optically coupled to the first surface of the transparent piezoelectric transducer, wherein the optical lens acts as a backing layer for improving a signal-to-noise ratio of the transparent piezoelectric transducer and is configured to transmit and shape a light beam to the target, wherein:
the optical lens is made of a material with a second acoustic impedance; and
the first and second acoustic impedances are substantially similar to minimize an acoustic impedance mismatch such that sensitivity of the device is improved.

2. The device of claim 1, wherein the optical lens is a gradient-index (GRIN) lens.

3. The device of claim 2, wherein the GRIN lens is designed for shaping the light beam as a focusing beam, a collimating beam, or a diverging beam by varying an index of refraction.

4. The device of claim 1, wherein the material is quartz, silica, or glass.

5. The device of claim 1, wherein the optical lens is adhesively attached to the first surface of the transparent piezoelectric transducer.

6. The device of claim 1, wherein the transparent electrically conductive coatings are made of indium tin oxide (ITO), tin oxide, indium oxide, zinc oxide, or any combination thereof.

7. The device of claim 1, wherein the transparent piezoelectric transducer is made of Lithium niobate (LNO), polyvinylidene fluoride (PVDF), lead magnesium niobate-lead titanate (PMN-PT), transparent polymers, transparent ceramics.

8. The device of claim 1, wherein:
the first surface is a flat surface and has a different curvature than the second surface; and
the second surface is a concave surface with a radius of curvature determined based on a focal length for focusing the acoustic waves from the target and emitting the acoustic waves from the transparent ultrasound transducer device.

9. The device of claim 1 further comprising a transparent housing arranged to house a transducer unit formed by contacting the optical lens to the first surface of the transparent piezoelectric transducer, wherein the transparent housing is made of glass or acrylic.

10. The device of claim 9 further comprising a parylene film coated as an outermost layer covering the transparent housing.

11. The device of claim 9 further comprising a transparent epoxy resin filling a gap between the transparent housing and the transducer unit.

12. The device of claim 1, wherein the optical lens is a focusing lens, a collimating lens, or a diverging lens.

13. A method for assembling a transparent ultrasound transducer device for multi-mode optical imaging on a target, the transparent ultrasound transducer device comprising a transparent piezoelectric transducer having a first surface and a second surface, and an optical lens, the method comprising the steps of:
processing a piezoelectric substrate to form the second surface with a concave surface, wherein the first surface is a flat surface and has a different curvature than the second surface;
coating the first surface and the second surface with transparent electrically conductive coatings;
contacting the optical lens with the transparent piezoelectric transducer to obtain a transducer unit; and
connecting one or more wires from the first surface and the second surface to external connectors.

14. The method of claim 13 further comprising the steps of:
assembling the transducer unit into a transparent housing; and
filling a gap between the transparent housing and the transducer unit with a transparent epoxy resin.

15. The method of claim 14 further comprising the step of coating the transparent housing with a parylene film as an outermost layer.

16. The method of claim 14, wherein the step of filling the gap with the transparent epoxy resin comprises the step of extracting gas from the transparent epoxy resin.

17. The method of claim 13, wherein the step of contacting the optical lens with the first surface of the transparent piezoelectric transducer comprises the step of adhesively attaching the optical lens to the first surface of the transparent piezoelectric transducer.

18. The method of claim 13, wherein the step of processing the piezoelectric substrate to form the second surface with the concave surface further comprises polishing the piezoelectric substrate to obtain the concave surface with a radius of curvature determined based on a focal length for focusing the acoustic waves from the target and emitting the acoustic waves from the transparent ultrasound transducer device.

19. The method of claim 13, wherein the one or more wires are connected to the first surface and the second surface using electrically conductive glue.

* * * * *